United States Patent
Gordon et al.

(10) Patent No.: US 9,220,928 B2
(45) Date of Patent: *Dec. 29, 2015

(54) **PLANT EXTRACTS FROM *ACRONYCHIA* SPECIES AND THEIR USE**

(75) Inventors: Victoria Anne Gordon, Yungaburra (AU); Paul Warren Reddell, Yungaburra (AU)

(73) Assignee: EcoBiotics Ltd, Yungaburra, Queensland (AU)

( * ) Notice: Subject to any disclaimer, the term of this patent is extended or adjusted under 35 U.S.C. 154(b) by 424 days.

This patent is subject to a terminal disclaimer.

(21) Appl. No.: 13/141,780

(22) PCT Filed: Dec. 23, 2009

(86) PCT No.: PCT/AU2009/001697

§ 371 (c)(1),
(2), (4) Date: Sep. 13, 2011

(87) PCT Pub. No.: WO2010/071941

PCT Pub. Date: Jul. 1, 2010

(65) Prior Publication Data

US 2011/0318439 A1    Dec. 29, 2011

(30) Foreign Application Priority Data

Dec. 24, 2008   (AU) ................................ 2008906633

(51) Int. Cl.

| | | |
|---|---|---|
| *A61K 36/75* | (2006.01) | |
| *A61Q 17/00* | (2006.01) | |
| *A23L 1/221* | (2006.01) | |
| *A23L 1/222* | (2006.01) | |
| *A23L 1/226* | (2006.01) | |
| *A23L 1/30* | (2006.01) | |
| *A61K 8/34* | (2006.01) | |
| *A61K 8/35* | (2006.01) | |
| *A61K 8/36* | (2006.01) | |
| *A61K 8/97* | (2006.01) | |
| *A61K 31/015* | (2006.01) | |
| *A61K 31/047* | (2006.01) | |
| *A61K 31/202* | (2006.01) | |
| *C07C 13/19* | (2006.01) | |
| *C07C 59/64* | (2006.01) | |
| *C11B 9/00* | (2006.01) | |

(52) U.S. Cl.
CPC ............... *A61Q 17/005* (2013.01); *A23L 1/222* (2013.01); *A23L 1/2215* (2013.01); *A23L 1/2265* (2013.01); *A23L 1/22635* (2013.01); *A23L 1/3002* (2013.01); *A61K 8/342* (2013.01); *A61K 8/355* (2013.01); *A61K 8/361* (2013.01); *A61K 8/97* (2013.01); *A61K 31/015* (2013.01); *A61K 31/047* (2013.01); *A61K 31/202* (2013.01); *A61K 36/75* (2013.01); *C07C 13/19* (2013.01); *C07C 59/64* (2013.01); *C11B 9/0015* (2013.01); *C11B 9/0034* (2013.01); *C11B 9/0049* (2013.01); *A61K 2800/522* (2013.01); *C07C 2101/14* (2013.01)

(58) Field of Classification Search
None
See application file for complete search history.

(56) References Cited

U.S. PATENT DOCUMENTS

| 4,939,171 A | 7/1990 | Moeller et al. | |
|---|---|---|---|
| 2007/0135526 A1* | 6/2007 | Huang | 514/693 |

FOREIGN PATENT DOCUMENTS

| CN | 101199498 A * | 6/2008 |
|---|---|---|
| EP | 0-869-118 A1 | 10/1998 |
| EP | 1 886 990 A1 | 2/2008 |
| JP | 2007230955 A | 9/2007 |
| WO | 2006/016912 A2 | 2/2006 |
| WO | 2006/094217 A2 | 9/2006 |
| WO | 2008/015241 A1 | 2/2008 |

OTHER PUBLICATIONS

Schellhorn (Liquid Crystals (1994), vol. 17, No. 4, pp. 529-542).*
De Silva (Phytochemistry (1991), vol. 30, No. 5, pp. 1709-1710).*
Registry entry for 1-ethenyl-1-methyl-2,4-bis(1-methylethenyl)cyclohexane—2013.*
Niculescu-Duvaz (Neoplasma (1991), vol. 38, No. 6, pp. 545-547).*
Han et al., "Isolation of 1-[2',4'-dihydroxy-3',5'-di-(3"-methylbut-2"-enyl)-6'-methoxy] phenylethanone from *Acronychia pedunculata* (L.) Miq. by high-speed counter-current chromatography," *Journal of Chromatography A* 1022(1-2): 213-216, Jan. 2, 2004 [abstract only: XP-002690924, one page].
Lesueur et al., "Composition and antimicrobial activity of the essential oil of *Acronychia pedunculata* (L.) Miq. from Vietnam," *Natural Product Research* 22(5): 393-398, Mar. 2008 [as reproduced in *Medicinal & Aromatic Plants Abstracts*, vol. 31(2), Apr. 1, 2009, Scientific Publishers, New Delhi, India, abstract only, one page].
Lichius et al., "Antimitotic and Cytotoxic Flavonols from *Zieridium pseudobtusifolium* and *Acronychia porter*," *Journal of Natural Products* 57(7): 1012-1016, Jul. 1994.
Pathmasiri et al., "Aryl Ketones from *Acronychia pedunculata* with Cyclooxygenase-2 Inhibitory Effects," *Chemistry & Biodiversity* 2(4): 463-469, Apr. 2005.

(Continued)

*Primary Examiner* — Susan Hoffman

(74) *Attorney, Agent, or Firm* — Seed IP Law Group PLLC

(57) ABSTRACT

The invention relates to plant extracts and bioactive molecules derived from the plant genus *Acronychia* and their use as antioxidants, antibacterials, anthelmintic, anti-inflammatories, cancer chemopreventatives, food additives and fragrance components in pharmaceuticals, nutraceuticals, foods and cosmetics.

2 Claims, 1 Drawing Sheet

(56) References Cited

OTHER PUBLICATIONS

SkinlightCo.uk: "Skin Brightening Fruit Fiesta Peel," retrieved from Internet, URL:http://www.skinlight.co.uk/product_845_Skin+Brightening+Fruit+Fiesta+Peel+.html, Jan. 1, 2006 [retrieved Jan. 21, 2013, 2 pages].

Svoboda et al., "Alkaloids of *Acronychia baueri* Schott I: Isolation of the Alkaloids and a Study of the Antitumor and Other Biological Properties of Acronycine," *Journal of Pharmaceutical Sciences* 55(8): 758-768, Aug. 1, 1966.

Sy et al., "1-[2',4'-Dihydroxy-3'-(3'-Methylbut-2'-enyl)-5'-(1'''-ethoxy-3'''-methylbutyl)-6'-methoxy]phenylethanone from *Acronychia pedunculata*," *Phytochemistry* 52(4): 681-683, Oct. 1, 1999.

Zhao et al., "Functional Properties of Australian Bushfoods," Rural Industries Research and Development Corporation, ISBN 1 74151 429 0, Pub. No. 07/030, Jan. 2007 (48 pages).

Marta et al. "Chroman carboxylic acids related to natural prenylated flavonoids and stilbenes", *Il Farmaco Ed Sc* 36(9):794-803. 1981. 10 Pages.

Yazawa et al. "Citronellyloxybenzene derivatives as ferroelectric liquid crystals", Accession No. 1992:480281 Caplus, 1992. 1 Page.

Schellhorn et al. "Synthesis and characterization of liquid crystalline monofunctionalized 'two chain' diols and corresponding low molecular weight siloxane derivatives", *Liquid Crystals* 17(4):529-42, 1994. 15 Pages.

Lindsay. "Where next for bush foods?", *West Australian Nut and Tree Crops Assoc 24*:63-8, 2000. 4 Pages.

Su et al. "Acetophenone derivatives from *Acronychia pedunculata*", *J Nat Prod* 66(7):990-3, 2003. 4 Pages.

Curini et al. "3-(4'-geranyloxy-3'-methoxyphenyl)-2-trans Propenoic acid: a novel promising cancer chemopreventive agent", *Anti-Cancer Agents in Med Chem* 6:571-7, 2006. 7 Pages.

Jayasinghe et al. "Screening for antimicrobial activity of *Acronychia pedunculata* (ankenda) and *Adenanthera pavonina* (madatiya) against bacteria causing skin and wound infections in humans", *Proceedings of the Peradeniya University Research Sessions, Sri Lanka 11*:105, Nov. 30, 2006. 1 Page.

Epifano et al. "Synthesis and anti-inflammatory activity of 3-(4'-geranyloxy-3'-methoxyphenyl)-2-trans propenoic acid and its ester derivatives", *Bioorg Med Chem Lett 17*:5709-14, 2007. 6 Pages.

Gardner et al. "Synthesis and transfection efficiencies of new lipophilic polyamines", *J Med Chem* 50(2):308-18, 2007. 11 Pages.

Rodrigo et al. "Antifungal, antioxidant and cytotoxic activity of *Acronychia pedunculata* and *Adenanthera pavonina*", *Proceedings of the Peradeniya University Research Sessions, Sri Lanka* 12(1):94-95, Nov. 30, 2007. 2 Pages.

Ishibe et al. "Fluorescent rare earth metal complexes, their manufacture, and solar cell", Accession No. 2007:1024877 Caplus, 2007. 2 Pages.

Bispo et al. "Main-chain liquid crystalline elastomers: monomer and cross-linker molecular control of the thermotropic and elastic properties", *Macromolecules* 41(9):3098-108, 2008. 11 Pages.

Bodet et al. "Effects of 3-(4'-geranyloxy-3'-methoxyphenyl)-2-trans propenoic acid and its ester derivatives on biofilm formation by two oral pathogens, *Porphyromonas gingivalis* and *Streptococcus mutans*", *Euro J Medicinal Chem 43*:1612-20, 2008. 9 Pages.

Epifano et al. "Neuroprotective effect of prenyloxycoumarins from edible vegetables", *Neurosci Lett 443*: 57-60, 2008. 4 Pages.

International Search Report, mailed Feb. 19, 2010, for PCT/AU2009/001697, 4 Pages.

Written Opinion, mailed Feb. 19, 2010, for PCT/AU2009/001697, 6 Pages.

International Preliminary Report on Patentability, mailed Apr. 27, 2011, for PCT/AU2009/001697, 14 Pages.

Richard et al. "Calculation of the thermodynamic properties at elevated temperatures and pressures of saturated and aromatic high molecular weight solid and liquid hydrocarbons in kerogen, bitumen, petroleum, and other organic matter of biogeochemical interest," *Geochimica et Cosmochimica Acta* vol. 62, No. 23/24, pp. 3591-3636, 1998. exerpt—pp. 3591 and 3629.

Zhou et al. "Chemical components of Arten is ia scoparia volatile oil and its poison activity to mosquito," *Chinese Journal of Applied Ecology* 17 (5), 907-910, May 2006. English abstract.

Zhang et al. "Two novel synthetic antioxidants for deep frying oils," *Food Chemistry 84*, 219-222, 2004. exerpt—pp. 219 and 221.

* cited by examiner

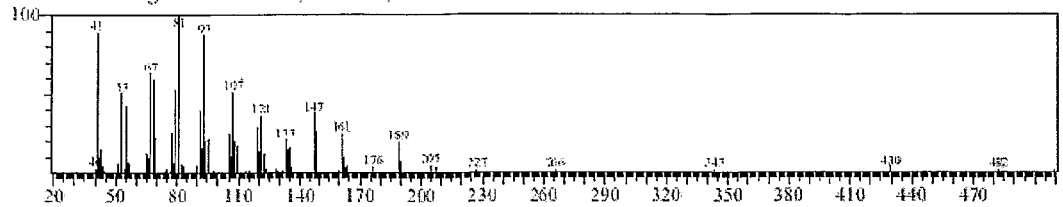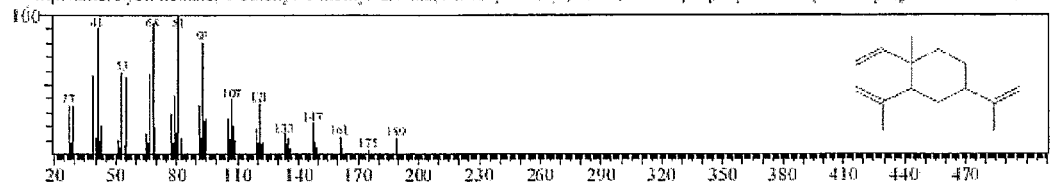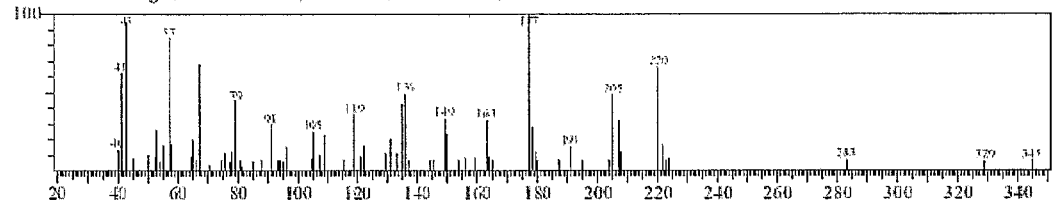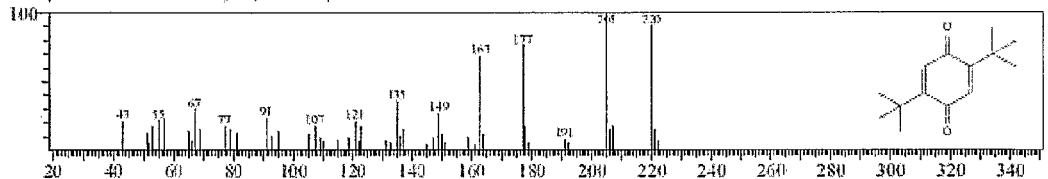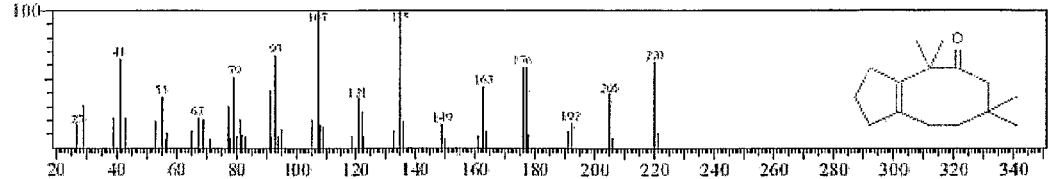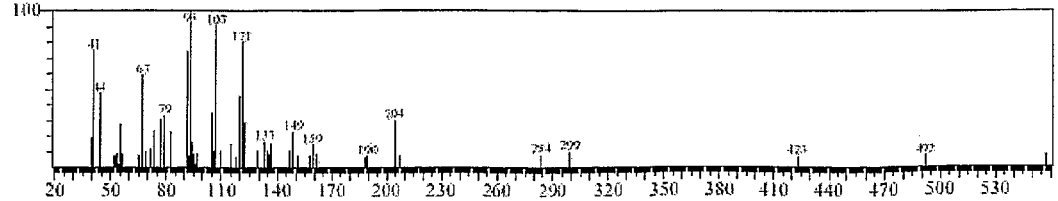

PLANT EXTRACTS FROM *ACRONYCHIA* SPECIES AND THEIR USE

FIELD OF THE INVENTION

The invention relates to plant extracts and bioactive molecules derived from the plant genus *Acronychia* and their use as antioxidants, antibacterials, anthelmintic, anti-inflammatories, cancer chemopreventatives, food additives and fragrance components in pharmaceuticals, nutraceuticals, foods and cosmetics.

BACKGROUND OF THE INVENTION

Biodiscovery is a field of endeavour that investigates and screens for bioactive natural products from natural environments such as plants, microorganisms, soils and marine life. In biodiscovery, biological materials are screened for molecules having properties which may be of therapeutic benefit for use in treatment of humans or animals, for use in cosmetic compositions, for use as food additives or fragrance components.

SUMMARY OF THE INVENTION

The present invention is predicated in part on the discovery that extracts of the fruit of *Acronychia* species have potent antibacterial, anthelmintic, antioxidant, anti-inflammatory and/or anti-cancer activity.

In a first aspect of the invention there is provided a method of treating or preventing a bacterial infection comprising administering to a subject an effective amount of an extract from an *Acronychia* species.

In a further aspect of the invention there is provided a method of treating or preventing a helminthic infection in a subject comprising administering an effective amount of an extract from an *Acronychia* species.

In another aspect of the invention there is provided a method of treating or preventing a cell proliferative disorder comprising administering to a subject an effective amount of an extract from an *Acronychia* species.

In another aspect of the invention there is provided a method of treating or preventing an inflammatory disease or disorder comprising administering to a subject an effective amount of an extract from an *Acronychia* species.

In a further aspect of the invention there is provided a method of treating or preventing a disease or disorder related to oxidative stress comprising administering to a subject an effective amount of an extract from an *Acronychia* species.

In yet another aspect of the invention there is provided a method of treating or preventing a bacterial infection comprising administering to a subject an effective amount of a compound of formula (I):

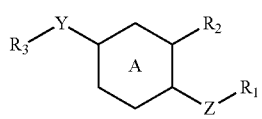

(I)

wherein A is an aryl group or a heteroaryl group;
Z is selected from —O—, —S— and —NR$_4$—;
Y is selected from a covalent bond and —(CH$_2$)$_p$—;
R$_1$ is selected from —C$_5$-C$_{20}$alkyl, —C$_5$-C$_{20}$alkenyl, —C$_5$-C$_{20}$alkynyl and —C$_3$-C$_8$cycloalkyl;
R$_2$ is selected from hydrogen, —C$_1$-C$_6$alkyl, —C$_2$-C$_6$alkenyl, —C$_2$-C$_6$alkynyl, —C$_3$-C$_8$cycloalkyl, hydroxy, —OC$_1$-C$_6$alkyl, —OC$_2$-C$_6$alkenyl, —OC$_2$-C$_6$alkynyl, —OC$_3$-C$_8$cycloalkyl, thiol, —SC$_1$-C$_6$alkyl, —SC$_2$-C$_6$alkenyl, —SC$_2$-C$_6$alkynyl, —SC$_3$-C$_8$cycloalkyl, —NR$_4$C$_1$-C$_6$alkyl, —NR$_4$C$_2$-C$_6$alkenyl, —NR$_4$C$_2$-C$_6$alkynyl and —NR$_4$C$_3$-C$_8$cycloalkyl;
R$_3$ is selected from —CO$_2$H or an isosteric equivalent of a carboxy group;
R$_4$ is selected from hydrogen and —C$_1$-C$_6$alkyl;
and p is an integer from 1 to 10; or a pharmaceutically salt thereof.

In yet another aspect of the invention there is provided a compound of formula (II):

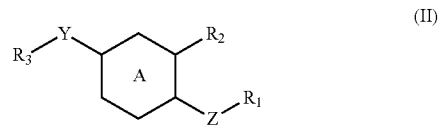

(II)

wherein A is an aryl group or a heteroaryl group;
Z is selected from —O—, —S— and —NR$_4$—;
Y is selected from a covalent bond and —(CH$_2$)$_p$—;
R$_1$ is selected from —C$_5$-C$_{20}$alkyl, —C$_5$-C$_{20}$alkenyl, —C$_5$-C$_{20}$alkynyl and —C$_3$-C$_8$cycloalkyl;
R$_2$ is selected from —C$_1$-C$_6$alkyl, —C$_2$-C$_6$alkenyl, —C$_2$-C$_6$alkynyl, —C$_3$-C$_8$cycloalkyl, hydroxy, —OC$_1$-C$_6$alkyl, —OC$_2$-C$_6$alkenyl, —OC$_2$-C$_6$alkynyl, —OC$_3$-C$_8$cycloalkyl, thiol, —SC$_1$-C$_6$alkyl, —SC$_2$-C$_6$alkenyl, —SC$_2$-C$_6$alkynyl, —SC$_3$-C$_8$cycloalkyl, —NR$_4$C$_1$-C$_6$alkyl, —NR$_4$C$_2$-C$_6$alkenyl, —NR$_4$C$_2$-C$_6$alkynyl and —NR$_4$C$_3$-C$_8$cycloalkyl;
R$_3$ is selected from —CO$_2$H or an isosteric equivalent of a carboxy group;
R$_4$ is selected from hydrogen and —C$_1$-C$_6$alkyl;
and p is an integer from 1 to 10; or a pharmaceutically salt thereof.

In a further aspect of the invention there is provided a pharmaceutical composition comprising an extract from *Acronychia* species or a compound of formula (I) or formula (II) and a pharmaceutically acceptable salt thereof.

In yet another aspect of the invention there is provided a flavour or fragrance composition comprising an extract from an *Acronychia* species, said extract comprising at least one of:
  1-ethenyl-1-methyl-2,4-bis(1-methylethenyl)cyclohexane,
  2,6-di-tert-butylbenzoquinone,
  2,5-di-tert-butyl-1,4-benzoquinone,
  Tetracontane-1,40-diol, and
  2,2,5,5-tetramethyl-bicyclo[6.3.0]undec-1(8)-enone.

In yet another aspect of the invention, there is provided a cosmetic, food or fragrance composition comprising an extract from an *Acronychia* species, wherein the extract is obtained by a method comprising initial water or alcohol extraction and a subsequent ethyl acetate extraction.

In a further aspect of the invention there is provided a use of an extract from an *Acronychia* species as a fragrance or flavour component in a food or other composition.

In another aspect of the invention there is provided the use of an extract of an *Acronychia* species as a food additive, a fragrance component or an antioxidant, an anti-inflammatory or an antibacterial component of a cosmetic composition.

DETAILED DESCRIPTION OF THE INVENTION

The plant genus *Acronychia* is a member of the citrus family (Ruticeae) and comprises approximately 50 species that occur naturally in Australia, the Pacific Islands, Malesia and Asia. Extracts from any of these species may be used in the invention. In some embodiments the extract is obtained from *Acronychia* species native to Australia including *A. aberrans, A. acidula, A. acronychioides, A. acuminate, A. baeuerlenii, A. chooreechillum, A. crassipetala, A. eungellensis, A. imperforate, A. laevis, A. littoralis, A. oblongifolia, A. octanara, A. parviflora, A. pauciflora, A. pubescens, A.* species (Batavia Downs), *A. suberosa, A. vestita* and *A. wilcoxiana*. In particular embodiments, the extract is obtained from *A. acidula, A. aberrans, A. acronychioides* or *A. crassipetala*, especially *A. acidula*.

The extract may be obtained from any part of the plant such as the fruit, the seed, the bark, the leaf, the flower, the roots and the wood. In particular embodiments, the extract is obtained from the fruit of the plant.

For example, biomass obtained from the fruit of the plant is subject to initial solvent extraction, for example with a polar solvent, for example water or an alcohol such as methanol or ethanol. The initial extraction is then concentrated and diluted with water and subject to extraction with a second solvent, for example, ethyl acetate. The solvent samples from the second extraction are pooled and subject to separation by preparative HPLC fractionation. The fractions are analysed by analytical HPLC and pooled according to the retention time of compounds found in the samples. The pooled fractions are weighed, bioassayed and analysed by analytical HPLC. Further fractionation using one or more preparative HPLC is performed to isolate specific compounds. Each compound is bioassayed and its structure identified by UV, NMR and mass spectrometric (LC and GC) techniques.

In one aspect of the invention there is provided a method of treating or preventing a bacterial infection comprising administering to a subject an effective amount of an extract from an *Acronychia* species.

In some embodiments, the extract is obtained from *A. acidula*.

The bacterial infection may be caused by a Gram positive or Gram negative bacteria, especially Gram positive bacteria including bacteria of the Genus *Bacillus* (e.g. *B. subtilis, B. anthracis, B. cereus, B. fermis, B. licheniformis, B. megaterium, B. pumilus, B. coagulans, B. pantothenticus, B. alvei, B. brevis, B. circulans, B. laterosporus, B. macerans, B. polymyxa, stearothermophilus, B. thuringiensis, B. sphaericus*), *Staphylococcus* (e.g. *S. aureus, S. epidermidis, S. haemolyticus, S. saprophyticus*), *Streptococcus* (e.g. *S. pyogenes, S. pneumoniae, S. agalactiae, S. pyogenes, S. agalactiae, S. dysgalactiae, S. equisimilis, S. equi, S. zooepidemicus, S. anginosus, S. salivarius, S. milleri, S. sanguis, S. mitior, S. mutans, S. faecalis, S. faecium, S. Bovis, S. equinus, S. uberus, S. avium*), *Aerococcus, Gemella, Corynebacterium, Listeria, Kurthia, Lactobacillus, Erysipelothrix, Arachnia, Actinomyces, Propionibacterium, Rothia, Bifidobacterium, Clostridium, Eubacterium, Nocardia, Mycobacterium*.

In some embodiments, specific compounds are obtained from the extract and used in the method of treating or preventing bacterial infections, or derivatives or analogues of such compounds are used. For example, suitable compounds obtained from the extract, derivatives or analogues of such compounds are compounds of formula (I):

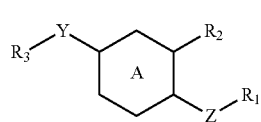

wherein A is an aryl group or a heteroaryl group;

Z is selected from —O—, —S— and —NR$_4$—;

Y is selected from a covalent bond and —(CH$_2$)$_p$—;

R$_1$ is selected from —C$_5$-C$_{20}$alkyl, —C$_5$-C$_{20}$alkenyl, —C$_5$-C$_{20}$alkynyl and —C$_3$-C$_8$cycloalkyl;

R$_2$ is selected from hydrogen, —C$_1$-C$_6$alkyl, —C$_2$-C$_6$alkenyl, —C$_2$-C$_6$alkynyl, —C$_3$-C$_8$cycloalkyl, hydroxy, —OC$_1$-C$_6$alkyl, —OC$_2$-C$_6$alkenyl, —OC$_2$-C$_6$alkynyl, —OC$_3$-C$_8$cycloalkyl, thiol, —SC$_1$-C$_6$alkyl, —SC$_2$-C$_6$alkenyl, —SC$_2$-C$_6$alkynyl, —SC$_3$-C$_8$cycloalkyl, —NR$_4$C$_1$-C$_6$alkyl, —NR$_4$C$_2$-C$_6$alkenyl, —NR$_4$C$_2$-C$_6$alkynyl and —NR$_4$C$_3$-C$_8$cycloalkyl;

R$_3$ is selected from —CO$_2$H or an isosteric equivalent of a carboxy group;

R$_4$ is selected from hydrogen and —C$_1$-C$_6$alkyl;

and p is an integer from 1 to 10; or a pharmaceutically salt thereof.

Particular compounds of formula (I) are compounds of formula (IA):

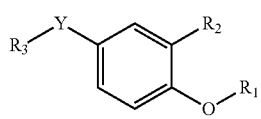

Y is selected from a covalent bond and —(CH$_2$)$_p$—;

R$_1$ is selected from —C$_5$-C$_{20}$alkyl, —C$_5$-C$_{20}$alkenyl and —C$_3$-C$_8$cycloalkyl;

R$_2$ is selected from hydrogen, —C$_1$-C$_6$alkyl, —C$_2$-C$_6$alkenyl, —C$_2$-C$_6$alkynyl, —C$_3$-C$_8$cycloalkyl, hydroxy, —OC$_1$-C$_6$alkyl, —OC$_2$-C$_6$alkenyl, —OC$_2$-C$_6$alkynyl and —OC$_3$-C$_8$cycloalkyl;

R$_3$ is selected from —CO$_2$H or an isosteric equivalent of a carboxy group; and p is an integer from 1 to 10; or a pharmaceutically salt thereof.

In particular embodiments of formula (I) one or more of the following applies:

A is an aryl group, especially phenyl,

Z is —O— or —S—, especially —O—;

Y is —(CH$_2$)$_p$— where p is 1 to 10, especially 1 to 6, more especially 1 to 4, most especially 2;

R$_1$ is —C$_5$-C$_{20}$alkyl or —C$_5$-C$_{20}$alkenyl, especially —C$_5$-C$_{20}$alkenyl, for example, —C$_5$-C$_{15}$alkenyl having 1 to 3 double bonds, especially —C$_{15}$alkenyl such as farnesyl;

R$_2$ is hydrogen, hydroxyl, —OC$_1$-C$_6$alkyl, —OC$_2$-C$_6$alkenyl and —OC$_3$-C$_8$cycloalkyl, especially hydrogen, hydroxyl or —OC$_1$-C$_6$alkyl, more especially hydrogen or —OC$_1$-C$_3$alkyl, most especially hydrogen or —OCH$_3$;

R$_3$ is —CO$_2$H.

Particularly useful compounds of formula (I) are:
3-(4-farnesyloxyphenyl)propionic acid

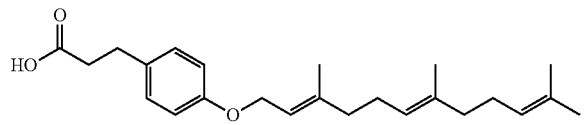 [SMILES: CC(C)=CCC/C(C)=C/CC/C(C)=C/COc1ccc(CCC(=O)O)cc1]

and
3-(4-farnesyloxy-3-methoxyphenyl)propionic acid

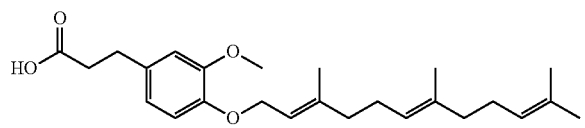 [SMILES: COc1cc(CCC(=O)O)ccc1OC/C=C(\C)CC/C=C(\C)CCC=C(C)C]

The term "alkyl" refers to optionally substituted linear and branched hydrocarbon groups having 1 to 20 carbon atoms. Where appropriate, the alkyl group may have a specified number of carbon atoms, for example, —$C_1$-$C_6$ alkyl which includes alkyl groups having 1, 2, 3, 4, 5 or 6 carbon atoms in linear or branched arrangements. Non-limiting examples of alkyl groups include methyl, ethyl, propyl, isopropyl, butyl, s- and t-butyl, pentyl, 2-methylbutyl, 3-methylbutyl, hexyl, heptyl, 2-methylpentyl, 3-methylpentyl, 4-methylpentyl, 2-ethylbutyl, 3-ethylbutyl, octyl, nonyl, decyl, undecyl, dodecyl, tridecyl, tetradecyl, pentadecyl and the like.

The term "alkenyl" refers to optionally substituted unsaturated linear or branched hydrocarbon groups, having 2 to 20 carbon atoms and having at least one double bond. Where appropriate, the alkenyl group may have a specified number of carbon atoms, for example, $C_2$-$C_6$ alkenyl which includes alkenyl groups having 2, 3, 4, 5 or 6 carbon atoms in linear or branched arrangements. Non-limiting examples of alkenyl groups include, ethenyl, propenyl, isopropenyl, butenyl, s- and t-butenyl, 3-methylbut-2-enyl, pentenyl, hexenyl, hept-1, 3-dienyl, hex-1,3-dienyl, hexa-1,3,5-trienyl, heptenyl, octenyl, 3,7-dimethyl-octa-2,6-dienyl, nonenyl, decenyl, undecenyl and farnesyl and the like.

The term "alkynyl" refers to optionally substituted unsaturated linear or branched hydrocarbon groups, having 2 to 20 carbon atoms and having at least one triple bond. Where appropriate, the alkynyl group may have a specified number of carbon atoms, for example, $C_2$-$C_6$ alkynyl groups have 2, 3, 4, 5 or 6 carbon atoms in linear or branched arrangements. Non-limiting examples of alkynyl groups include ethynyl, propynyl, butynyl, pentynyl, hexynyl and the like.

The terms "cycloalkyl" refer to optionally substituted saturated or unsaturated monocyclic, bicyclic or tricyclic carbon groups. Where appropriate, the cycloalkyl group may have a specified number of carbon atoms, for example, $C_3$-$C_6$ cycloalkyl is a carbocyclic group having 3, 4, 5 or, 6 carbon atoms. Non-limiting examples may include cyclopropyl, cyclobutyl, cyclopentyl, cyclopentenyl, cyclohexyl, cyclohexenyl, cyclohexadienyl, cycloheptyl and cyclooctyl and the like.

"Aryl" means a $C_6$-$C_{10}$ membered monocyclic or bicyclic carbocyclic ring system having up to 7 atoms in each ring, wherein at least one ring is aromatic. Examples of aryl groups include, but are not limited to, phenyl, naphthyl and tetrahydronaphthyl. The aryl may comprise 1-2 benzene rings. If two aromatic rings are present, then the rings may be fused together, so that adjacent rings share a common bond.

The term "heteroaryl" as used herein means a stable monocyclic or bicyclic ring of up to 7 atoms in each ring, wherein at least one ring is aromatic and at least one ring contains from 1-4 heteroatoms, selected from sulfur, oxygen and nitrogen. Heteroaryl includes, but is not limited to, oxazolyl, thiazolyl, thienyl, furyl, 1-isobenzofuranyl. pyrrolyl, imidazolyl, pyrazolyl, isothiazolyl, isooxazolyl, pyridyl, pyrazinyl, pyrimidinyl, pyradazinyl, indolizinyl, isoindolyl, indolyl, purinyl, phthalazinyl, 1,2,3-triazolyl, 1,2,4-triazolyl, 1,2,3-oxadiazoyl, 1,2,4-oxadiazolyl, 1,2,5-oxadiazolyl 1,3,4-oxadiazolyl, 1,2,3,4-oxatriazolyl, 1,2,3,5-oxatriazolyl, 1,3,5-triazinyl, 1,2,4-triazinyl, 1,2,3-triazinyl, benzofuranyl, isobenzofuranyl, thionaphthenyl, isothionaphthenyl, indoleninyl, 2-isobenzazolyl, 1,5-pyrindinyl, pyrano[3,4-b]pyrrolyl, isoindazolyl, indoxazinyl, benzoxazolyl, quinolinyl, isoquinolinyl, cinnolinyl, quinazolinyl, naphthyridinyl, pyrido[3,4-b]pyridinyl, pyrido[3,2-b]pyridinyl, pyrido[4,3-b]pyridinyl, acridinyl, carbazolyl, quinoaxalinyl, pyrazolyl, benzotriazolyl, thiophenyl, isoquinolinyl, pyridinyl, tetrahydroquinolinyl, benzazepinyl, benzodioxanyl, benzoxepinyl, benzodiazepinyl, benzothiazepinyl and benzothiepinyl and the like.

The term "isosteric equivalent of a carboxy group" refers to a group which is physiochemically or topologically similar to carboxylic acid or carboxylate group. Examples of suitable carboxylic acid or carboxylate isosteres include, but are not limited to, tetrazole, tetrazolate, —CONH-tetrazole, oxidiazole, phosphate (—$PO_3H_2$), N-(aryl or heteroaryl)-sulfonamides, acylsulfonamides and sulfonic acid (—$SO_3H$) (See Patani and LaVoie, 1996 *Chem Rev.* 96:3147-3176).

The alkyl, alkenyl, alkynyl, cycloalkyl, aryl and heteroaryl groups may be substituted with one or more substituent independently selected from —F, —Cl, —Br, —I, —$CO_2$R, —CN, —OR, —SR, —N(R)$_2$, —NO$_2$, —NROR, —ON(R)$_2$, —SOR, —$SO_2$R, —$SO_3$R, —SON(R)$_2$, —$SO_2$N(R)$_2$, —$SO_3$N(R)$_2$, —P(R)$_3$, —P(=O)(R)$_3$, —OSi(R)$_3$, —OB(R)$_2$ wherein R is selected from hydrogen, —$C_1$-$C_{20}$ alkyl, —$C_2$-$C_{20}$ alkenyl, —$C_2$-$C_{20}$ alkynyl, —$C_3$-$C_8$ cycloalkyl, aryl, heteroaryl, heterocyclyl, arylalkyl, heteroarylalkyl, heterocyclylalkyl, —$C_1$-$C_{10}$ haloalkyl, —$C_1$-$C_{10}$ dihaloalkyl and —$C_1$-$C_{10}$ trihaloalkyl.

The term "halo" refers to fluorine (fluoro), chlorine (chloro), bromine (bromo) and iodine (iodo).

"Heterocyclic" or "heterocyclyl" refers to a non-aromatic ring having 3 to 8 atoms in the ring and of those atoms 1 to 4 are heteroatoms, said ring being isolated or fused to a second ring selected from 3- to 7-membered alicyclic ring containing 0 to 4 heteroatoms, wherein said heteroatoms are independently selected from O, N and S. Heterocyclic includes partially and fully saturated heterocyclic groups. Heterocyclic systems may be attached to another moiety via any number of carbon atoms or heteroatoms of the radical and may be both saturated and unsaturated, which includes all forms of carbohydrate moieties. Non-limiting examples of heterocyclic include pyrrolidinyl, pyrrolinyl, pyranyl, piperidinyl, piperazinyl, morpholinyl, tetrahydrofuranyl, tetrahydrothiophenyl, pyrazolinyl, dithiolyl, oxathiolyl, dioxanyl, dioxinyl, oxazinyl, azepinyl, diazepinyl, thiazepinyl, oxepinyl and thiapinyl, imidazolinyl, thiomorpholinyl, and the like.

The term "salt" as used herein includes pharmaceutically acceptable salts and those considered to be suitable for ingestion by humans and animals. Examples of suitable salts include alkali and alkaline earth metal salts, ammonium, aluminium, iron, amine, glucosamine, chloride, sulfate, sulfonate, bisulphate, nitrate, citrate, tartrate, bitartrate, phosphate, carbonate, bicarbonate, malate, maleate, napsylate, fumarate, succinate, acetate, benzoate, terephthalate, palmoate, pectinate, piperazine and S-methylmethionine salts and the like.

In another aspect of the invention, there is provided a compound of formula (II):

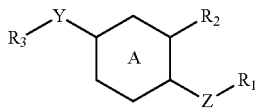

(II)

wherein A is an aryl group or a heteroaryl group;
Z is selected from —O—, —S— and —NR$_4$—;
Y is selected from a covalent bond and —(CH$_2$)$_p$—;
R$_1$ is selected from —C$_5$-C$_{20}$alkyl, —C$_5$-C$_{20}$alkenyl, —C$_5$-C$_{20}$alkynyl and —C$_3$-C$_8$cycloalkyl;
R$_2$ is selected from —C$_1$-C$_6$alkyl, —C$_2$-C$_6$alkenyl, —C$_2$-C$_6$alkynyl, —C$_3$-C$_8$cycloalkyl, hydroxy, —OC$_1$-C$_6$alkyl, —OC$_2$-C$_6$alkenyl, —OC$_2$-C$_6$alkynyl, —OC$_3$-C$_8$cycloalkyl, thiol, —SC$_1$-C$_6$alkyl, —SC$_2$-C$_6$alkenyl, —SC$_2$-C$_6$alkynyl, —SC$_3$-C$_8$cycloalkyl, —NR$_4$C$_1$-C$_6$alkyl, —NR$_4$C$_2$-C$_6$alkenyl, —NR$_4$C$_2$-C$_6$alkynyl and —NR$_4$C$_3$-C$_8$cycloalkyl;
R$_3$ is selected from —CO$_2$H or an isosteric equivalent of a carboxy group;
R$_4$ is selected from hydrogen and —C$_1$-C$_6$alkyl;
and p is an integer from 1 to 10; or a pharmaceutically salt thereof.

Particular compounds of formula (II) include compounds of formula (IIA):

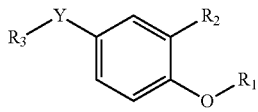

(IIA)

Y is selected from a covalent bond and —(CH$_2$)$_p$—;
R$_1$ is selected from —C$_5$-C$_{20}$alkyl, —C$_5$-C$_{20}$alkenyl and —C$_3$-C$_8$cycloalkyl;
R$_2$ is selected from —C$_1$-C$_6$alkyl, —C$_2$-C$_6$alkenyl, —C$_2$-C$_6$alkynyl, —C$_3$-C$_8$cycloalkyl, hydroxy, —OC$_1$-C$_6$alkyl, —OC$_2$-C$_6$alkenyl, —OC$_2$-C$_6$alkynyl and —OC$_3$-C$_8$cycloalkyl;
R$_3$ is selected from —CO$_2$H or an isosteric equivalent of a carboxy group;
p is an integer from 1 to 10; or a pharmaceutically salt thereof.

In particular embodiments of formula (II) one or more of the following applies:
A is an aryl group, especially phenyl,
Z is —O— or —S—, especially —O—;
Y is —(CH$_2$)$_p$— where p is 1 to 10, especially 1 to 6, more especially 1 to 4, most especially 2;
R$_1$ is —C$_5$-C$_{20}$alkyl or —C$_5$-C$_{20}$alkenyl, especially —C$_5$-C$_{20}$alkenyl, for example, —C$_5$-C$_{15}$alkenyl having 1 to 3 double bonds, especially —C$_{15}$alkenyl such as farnesyl;
R$_2$ is hydroxyl, —OC$_1$-C$_6$alkyl, —OC$_2$-C$_6$alkenyl and —OC$_3$-C$_8$cycloalkyl, especially hydroxyl or —OC$_1$-C$_6$alkyl, more especially —OC$_1$-C$_3$alkyl, most especially —OCH$_3$;
R$_3$ is —CO$_2$H.

A particular compound of formula (II) is 3-(4-farnesyloxy-3-methoxyphenyl)propionic acid

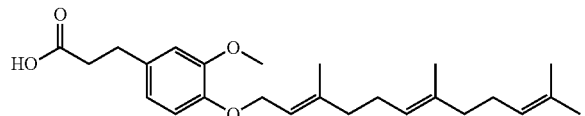

While some of the compounds of formula (I) or (II) may be obtained by extraction, others may be obtained by manipulation of isolated compounds or by synthesis from suitable starting materials.

For example, compounds of formula (1) or (II) in which Z is oxygen and R$_1$ is other than farnesyl may be obtained by hydrolysing the ether farnesyl group and replacing it with another alkyl, alkenyl, alkynyl or cycloalkyl group.

The alkenylene chain, Y, may be extended by nucleophilic addition with a protected carboxy alkyl group to the carboxy group R$_3$ followed by reduction and elimination of the resulting hydroxyl group, deprotection of the protected carboxyalkyl group may then be performed.

A person skilled in the art would be able to determine suitable conditions for obtaining derivatives of isolated compounds, for example, by reference to texts relating to synthetic methodology, examples of which are Smith M. B. and March J., March's Advanced Organic Chemistry, Fifth Edition, John Wiley & Sons Inc., 2001 and Larock R. C., Comprehensive Organic Transformations, VCH Publishers Ltd., 1989. Furthermore, selective manipulations of functional groups may require protection of other functional groups. Suitable protecting groups to prevent unwanted side reactions are provided in Green and Wuts, Protective Groups in Organic Synthesis, John Wiley & Sons Inc., 3$^{rd}$ Edition, 1999.

In a further aspect of the invention there is provided a method of treating or preventing a helminthic infection in a subject comprising administering an effective amount of an extract from an *Acronychia* species.

In preferred embodiments, the helminth (worm) is a nematode, trematode or cestode, especially *Haemonchus contortus, Trichinella spiralis, H. placei, Bursaphelenchus xylophilus, Ostertagia circumcincta, O. ostertagi, Mecistocirrus digitatus, Trychostrongylus axei, Trichuris trichiura, T. vulpis, T campanula, T suis, T ovis, Bunostomum trigonocephalum, B. phleboyomum, Oesophagostomum columbianum, O. radiatum, Cooperia curticei, C. punctata, C. oncophora, C. pectinata, Strongyloides papillosus, Chabertia ovina, Ancylostoma duodenale, A. braziliense. A. tubaeforme, A. caninum, Ascaris lumbricoides, Enterobius vermicularis, E. gregorii, Ascaris lumbricoides, Paragonimus Westermani, Clonorchis sinensis, Fasciola hepatica, Taenia solium, T. saginata, Capillaria aerophila, Necator americanus*, species of the genus *Trichuris, Baylisascaris, Aphelenchoides, Meliodogyne, Heterodera, Globodera, Nacobbus, Pratylenchus, Ditylenchus, Xiphinema, Longidorus, Trichodorus, Nematodirus*.

In another aspect of the invention there is provided a method of treating or preventing a cell proliferative disorder comprising administering to a subject an effective amount of an extract obtained from an *Acronychia* species.

In some embodiments, the cell proliferative disorder is a cancer, especially where the cancer is selected from leukaemia, melanoma, prostate cancer, breast cancer, ovarian cancer, basal cell carcinoma, squamous cell carcinoma, fibrosarcoma, colon cancer, lung cancer, a neoplasm and other solid tumour cancers. In other embodiments, the cell proliferative disorder is a non-malignant, for example, benign prostatic hyperplasia.

In yet another embodiment of the present invention there is provided a method of treating or preventing an inflammatory disorder comprising administering to a subject an effective amount of an extract from and *Acronychia* species.

In some embodiments of this aspect the inflammatory disorder is general inflammation, rheumatoid arthritis, colitis, bacterial sepsis or a disorder associated with a malfunctioning immune system, such as an autoimmune disorder. In some embodiments, the inflammatory disorder is bacterial sepsis. In some embodiments, the compound of the invention is capable of immunomodulation, especially immunosuppression. The compounds of the invention are also useful as immunosuppressive agents in organ transplantation.

In another aspect there is provided a method of treating or preventing a disease or disorder related to oxidative stress comprising administering to a subject an effective amount of an extract from an *Acronychia* species.

In some embodiments the disease or disorder related to oxidative stress is a disease or disorder which a subject may benefit from taking antioxidants. For example antioxidants are beneficial in treating or preventing cardiovascular disease, such as heart failure, heart attack and stroke; infectious diseases such as HIV/AIDS, and hepatitis; cancer; aging diseases such as arthritis, macular degeneration, glaucoma and cataracts; Lung diseases such as emphysema, chronic obstructive pulmonary disease (COPD) and adult respiratory distress syndrome; and neurological or neurodegenerative disorders such as Alzheimer's disease, Parkinson's disease, multiple sclerosis, Huntington's disease, dementia and cognitive decline, especially cognitive decline in companion animals such as dogs.

In some embodiments, the extract from *Acronychia* species is an anti-inflammatory antioxidant composition. This is particularly useful for the treatment of neurological disorders such as Alzheimer's disease.

In some embodiments the extract may be in the form of a nutraceutical composition that boosts the subject's antioxidant defences. The nutraceutical composition may be taken as a supplement while the subject is suffering from a disease or disorder or may be taken as a preventative measure to prevent or delay onset of a disease or disorder related to oxidative stress.

The extract of *Acronychia* species may be administered to any subject in need of treatment for a bacterial infection, a cell proliferative disorder, an inflammatory disease or a disease or disorder related to oxidative stress or to a subject who is in need of prevention of any of these disorders. The term "subject" as used herein includes humans, primates, livestock animals (eg. sheep, pigs, cattle, horses, donkeys), laboratory test animals (eg. mice, rabbits, rats, guinea pigs), companion animals (eg. dogs, cats), birds (eg. chickens, ducks, geese, parrots, cockatoos, pigeons, finches, raptors, ratites, quail, canaries), captive wild animals (eg. foxes, kangaroos, deer) and reptiles (eg. lizards and snakes). In some embodiments, the subject is human, a companion animal, a livestock animal or a laboratory test animal. In particular embodiments, the subject is a human, a companion animal or livestock animal.

An effective amount of the extract will be dependent on the extraction procedure and the source of the extract, that is, the *Acronychia* species used and whether the extract contains predominantly one compound or contains many compounds. An "effective amount" means an amount necessary at least partly to attain the desired response, or to delay the onset or inhibit progression or halt altogether, the onset or progression of a particular condition being treated. The amount varies depending upon the health and physical condition of the individual to be treated, the taxonomic group of individual to be treated, the degree of protection desired, the formulation of the composition, the assessment of the medical situation, and other relevant factors. It is expected that the amount will fall in a relatively broad range that can be determined through routine trials. An effective amount in relation to a human patient, for example, may lie in the range of about 0.1 ng per kg of body weight to 1 g per kg of body weight per dosage. The dosage is preferably in the range of 1 µg to 1 g per kg of body weight per dosage, such as is in the range of 1 mg to 1 g per kg of body weight per dosage. In one embodiment, the dosage is in the range of 1 mg to 500 mg per kg of body weight per dosage. In another embodiment, the dosage is in the range of 1 mg to 250 mg per kg of body weight per dosage. In yet another embodiment, the dosage is in the range of 1 mg to 100 mg per kg of body weight per dosage, such as up to 50 mg per kg of body weight per dosage. In yet another embodiment, the dosage is in the range of 1 µg to 1 mg per kg of body weight per dosage. Dosage regimes may be adjusted to provide the optimum therapeutic response. For example, several divided doses may be administered daily, weekly, monthly or other suitable time intervals, or the dose may be proportionally reduced as indicated by the exigencies of the situation.

Reference herein to "treatment" and "prophylaxis" is to be considered in its broadest context. The term "treatment" does not necessarily imply that a subject is treated until total recovery. Similarly, "prophylaxis" does not necessarily mean that the subject will not eventually contract a disease condition. Accordingly, treatment and prophylaxis include amelioration of the symptoms of a particular condition or preventing or otherwise reducing the risk of developing a particular condition. The term "prophylaxis" may be considered as reducing the severity or onset of a particular condition. "Treatment" may also reduce the severity of an existing condition.

In another embodiment there is provided a use of an extract from an *Acronychia* species in the manufacture of a medicament for treating or preventing a bacterial infection, a helmintic infection, a cell proliferative disorder, an inflammatory disease or disorder or a disorder related to oxidative stress.

In yet another embodiment there is provided a use of a compound of formula (I):

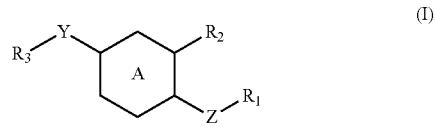

wherein A is an aryl group or a heteroaryl group;
Z is selected from —O—, —S— and —NR$_4$—;
Y is selected from a covalent bond and —(CH$_2$)$_p$—;
R$_1$ is selected from —C$_5$-C$_{20}$alkyl, —C$_5$-C$_{20}$alkenyl, —C$_5$-C$_{20}$alkynyl and —C$_3$-C$_8$cycloalkyl;
R$_2$ is selected from hydrogen, —C$_1$-C$_6$alkyl, —C$_2$-C$_6$alkenyl, —C$_2$-C$_6$alkynyl, —C$_3$-C$_8$cycloalkyl; hydroxy, —OC$_1$-C$_6$alkyl, —OC$_2$-C$_6$alkenyl, —OC$_2$-C$_6$alkynyl, —OC$_3$-C$_8$cycloalkyl, thiol, —SC$_1$-C$_6$alkyl, —SC$_2$-C$_6$alkenyl, —SC$_2$-C$_6$alkynyl, —SC$_3$-C$_8$cycloalkyl, —NR$_4$C$_1$-C$_6$alkyl, —NR$_4$C$_2$-C$_6$alkenyl, —NR$_4$C$_2$-C$_6$alkynyl and —NR$_4$C$_3$-C$_8$cycloalkyl;
R$_3$ is selected from —CO$_2$H or an isosteric equivalent of a carboxy group;
R$_4$ is selected from hydrogen and —C$_1$-C$_6$alkyl;

and p is an integer from 1 to 10; or a pharmaceutically salt thereof in the manufacture of a medicament for treating or preventing a bacterial infection.

In some embodiments the extract may be incorporated into a nutraceutical composition intended to improve the health and wellbeing of a subject. In some embodiments the nutraceutical composition is an antioxidant nutraceutical composition.

While it is possible that the extract may be used in a method in neat form, for example, as a dried powder, it is possible that the extract is formulated in a pharmaceutical or nutraceutical composition with a pharmaceutically acceptable carrier, diluent and/or excipient.

Dosage form and rates for pharmaceutical use and compositions are readily determinable by a person of skill in the art.

Dosage forms include tablets, dispersions, suspensions, injections, solutions, syrups, troches, capsules, suppositories, aerosols, transdermal patches and the like. These dosage forms may also include injecting or implanting devices designed specifically for, or modified to, controlled release of the pharmaceutical composition. Controlled release of the therapeutic agent may be effected by coating the same, for example, with hydrophobic polymers including acrylic resins, waxes, higher aliphatic alcohols, polylactic and polyglycolic acids and certain cellulose derivates such as hydroxypropylmethyl cellulose. In addition, the controlled release may be affected by using other polymer matrices, liposomes and/or microspheres.

Pharmaceutically acceptable carriers for systemic administration may also be incorporated into the compositions of this invention.

Suitably, the pharmaceutical composition comprises a pharmaceutically acceptable excipient. By "pharmaceutically acceptable excipient" is meant a solid or liquid filler, diluent or encapsulating substance that may be safely used in systemic administration. Depending upon the particular route of administration, a variety of carriers, well known in the art may be used. These carriers or excipients may be selected from a group including sugars, starches, cellulose and its derivates, malt, gelatine, talc, calcium sulphate, vegetable oils, synthetic oils, polyols, alginic acid, phosphate buffered solutions, emulsifiers, isotonic saline, and pyrogen-free water.

Any suitable route of administration may be employed for providing a human or non-human with the pharmaceutical composition of the invention. For example, oral, rectal, parenteral, sublingual, buccal, intravenous, intraarticular, intra-muscular, intra-dermal, subcutaneous, inhalational, intraocular, intraperitoneal, intracerebroventricular, transdermal and the like may be employed.

Pharmaceutical compositions of the present invention suitable for administration may be presented in discrete units such as vials, capsules, sachets or tablets each containing a predetermined amount of one or more pharmaceutically active compounds of the invention, as a powder or granules or as a solution or a suspension in an aqueous liquid, a non-aqueous liquid, an oil-in-water emulsion or a water-in-oil emulsion. Such compositions may be prepared by any of the method of pharmacy but all methods include the step of bringing into association an extract or one or more pharmaceutically active compounds of the invention with the carrier which constitutes one or more necessary ingredients. In general, the compositions are prepared by uniformly and intimately admixing the agents of the invention with liquid carriers or finely divided solid carriers or both, and then, if necessary, shaping the product in to the desired presentation.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the extract or active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component or extract, with or without carriers, is surrounded by a carrier, which is thus in association with it. Similarly, cachets and lozenges are included. Tablets, powders, capsules, pills, cachets, and lozenges can be used as solid forms suitable for oral administration.

Liquid form preparations include solutions, suspensions, and emulsions, for example, water or water-propylene glycol solutions. For example, parenteral injection liquid preparations can be formulated as solutions in aqueous polyethylene glycol solution.

The extract or compounds may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component or extract in water and adding suitable colorants, flavours, stabilizing and thickening agents, as desired.

Aqueous suspensions suitable for oral use can be made by dispersing the finely divided active component or extract in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component or extract, colorants, flavours, stabilizers, buffers, artificial and natural sweeteners, dispersants, thickeners, solubilizing agents, and the like.

For topical administration to the epidermis the extract or compounds may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Formulations suitable for topical administration in the mouth include lozenges comprising active agent or extract in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump. To improve nasal delivery and retention the compounds or extract may be encapsulated with cyclodextrins, or formulated with their agents expected to enhance delivery and retention in the nasal mucosa.

Administration to the respiratory tract may also be achieved by means of an aerosol formulation in which the active ingredient or extract is provided in a pressurized pack with a suitable propellant such as a chlorofluorocarbon (CFC) for example, dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound or extract in a suitable powder base such as lactose, starch, starch derivatives such as hydroxypropylmethyl cellulose and polyvinylpyrrolidone (PVP).

Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound or extract will generally have a small particle size for example of the order of 1 to 10 microns or less. Such a particle size may be obtained by means known in the art, for example by micronization.

In yet another aspect of the invention, there is provided the use of an extract from an *Acronychia* species in the manufacture of a medicament for treating or preventing a bacterial infection, a cell proliferative disorder, an inflammatory disease or disorder or a disease or disorder related to oxidative stress.

In another aspect of the invention the extract from *Acronychia* species may be incorporated into a cosmetic composition for its antibacterial, anti-inflammatory and/or antioxidant properties.

Suitable cosmetic compositions include face creams, body lotions, hand creams, foundation, anti-aging and anti-wrinkle formulations, face washes and peels, make-up removal compositions and the like.

Formulation of cosmetic compositions including antioxidant and/or antibacterial components is known in the art.

In a further aspect of the invention there is provided a cosmetic composition comprising an extract from an *Acronychia* species, wherein the extract is obtained by a method comprising initial water or alcohol extraction and a subsequent ethyl acetate extraction.

In another aspect of the invention, the extract of an *Acronychia* species is used as a food additive, a fragrance component or an antioxidant or antibacterial component of a cosmetic composition.

The extracts from *Acronychia* species have volatile components which provide flavour and fragrances. These volatile components may be used as a food additive in foods such as jams, ice cream, confectionary and sauces. Alternatively, the extract containing volatile components may be used as a fragrance in perfumes, cosmetics, household products such as cleaners, deoderisers or fabric softeners or in personal care products such as talcum powder, deodorants, soaps, shampoos, conditioners and the like.

The formulation of such household products or personal care products containing fragrances is well known in the art. For example, the extract may be included in the household product or personal care product in an amount in the range of 2-5%.

A number of volatile compounds were isolated from the extract of *A. acidula* as shown in FIG. 1. Compounds identified include 1-ethenyl-1-methyl-2,4-bis(1-methylethenyl)cyclohexane, 2,6-di-tert-butylbenzoquinone, 2,5-di-tert-butyl-1,4-benzoquinone, Tetracontane-1,40-diol, and 2,2,5,5-tetramethyl-bicyclo[6.3.0]undec-1(8)-enone. Smaller amounts of unidentified volatile components were also found by mass spectrometry.

Volatile components of the extract may be isolated by methods known in the art such as distillation, supercritical fluid extraction (SPE), microwave assisted extraction (MAE), solvent extraction, pressurised liquid extraction (PLE), ultrasonic extraction and solid phase extraction.

In another aspect. of the present invention there is provided a flavour or fragrance composition comprising one or more of the following compounds:
  1-ethenyl-1-methyl-2,4-bis(1-methylethenyl)cyclohexane,
  2,6-di-tert-butylbenzoquinone,
  2,5-di-tert-butyl-1,4-benzoquinone,
  Tetracontane-1,40-diol, and
  2,2,5,5-tetramethyl-bicyclo[6.3.0]undec-1(8)-enone.

In some embodiments, the flavour or fragrance composition contains at least two of the components listed above. In some embodiments the flavour or fragrance composition contains all of the components listed above.

BRIEF DESCRIPTION OF THE DRAWINGS

FIG. 1 provides mass spectrometric traces of minor volatile compounds present in an *A. acidula* extract.

In order that the invention be readily understood and put into practical effect, particular embodiments will now be described by way of the following non-limiting examples.

EXAMPLES

Screening Procedures
Antioxidant Activity
  DPPH Assay for radical scavenging
Background
  This assay is based upon the use of the stable free radical DPPH, which is a deep violet colour. When a solution of DPPH is mixed with that of a substance that can donate a hydrogen atom (e.g. an antioxidant), it gives rise to the reduced form of DPPH, with the loss of this violet colour.
Materials
2,2-Diphenyl-1-picryl-hydrazyl (DPPH); MW:394
Ethanol
Sample to be assayed at dilutions required
VERSAmax tunable microplate reader—Molecular Devices
Method
  1. A 0.1 mM solution of DPPH in ethanol (3.94 mg of DPPH in 100 mL of Ethanol) was prepared. Alternatively (If serial dilutions are to be done in the plate) a 10× solution of DPPH (1 mM, 3.94 mg in 10 mL ethanol) was prepared. Solutions were stored at 4° C. for a few weeks but lose colour over time.
2. 90 μL of 1× DPPH solution was added to each well used in the 96-well plate.
3. 10 μL of sample to be assayed was added to the wells containing DPPH (for a final dilution of 1/10) or 10 μL of a dilution of sample. Each sample was assayed in triplicate. A negative control of 10 μL ethanol was used replacing the sample. A positive control of a known concentration of catechin was used if required. If samples were coloured, control wells of ethanol and 10 μL of sample were used as colour blanks.
4. If serial dilutions of sample are performed in the plate, 90 μL of ethanol was added to the wells. 10 μL of sample was added to the top well and serially diluted 10 μL down the plate, removing 10 μL from the last well diluted to ensure an equal amount in each well. 10 μL of 10× DPPH, was added to each well.
5. After combining sample and DPPH, plates were left at room temp for 20 minutes before reading on the plate reader at a wavelength of 517 nm.

Lipid Peroxidation in Human Plasma
Background

Inhibition of lipid peroxidation is a major target for antioxidants. It has been shown by Itoh et al. 2004, *Biochemical Pharmacology*, 68, 813-818 (and references cited therein) that the free radical-mediated oxidation of human plasma in vitro generates cholesteryl ester hydroperoxide (CEOOH) as a major product, with smaller amounts of cholesteryl ester hydroxide (CEOH) and phospholipid hydro(per)oxide. Consequently, the extent of lipid peroxidation in plasma can be estimated from the formation of cholesteryl ester hydroperoxide (CEOOH).

Method

The effect of samples in reducing lipid peroxidation in dialysed human plasma was performed following the method of Itoh et al. 2004. Briefly this involved:
1. Blood was collected in ethylenediaminetetraacetic acid (EDTA) containing tubes from healthy volunteer after overnight fasting. Plasma was obtained by centrifugation at 1580×g for 10 min at 4° C. The plasma was dialyzed using a dialysis membrane for 18 h at 4° C. in PBS to eliminate ascorbic acid and other water-soluble small molecular weight antioxidants that were present.
2. Lipophilic 2,2'-azobis-(4-methoxy-2,4-dimethylvaleronitrile) (MeO-AMVN) (final concentration 0.2 mM) was added to PBS solution containing 10 volume % of dialyzed human plasma with and without 6.66 volume % of sample solution and the mixture was incubated at 37° C. for 1 hr.
3. Lipid peroxidation products were extracted with chloroform/methanol (2/1 by volume) and the chloroform layer analyzed. Cholesteryl ester hydroperoxide (CEOOH) and cholesteryl ester hydroxide (CEOH) were measured at 234 nm by HPLC with a spectrophotometric detector using an ODS column (Wakosil-II 5C18RS, 5 um, 250 mm×4.6 mm) with acetonitrile/isopropyl alcohol/water (44/54/2 by volume) eluted at 1 mL/min.

Antibacterial Assays
Overview

The bacteria used in these studies were:
*Streptococcus salivarius* K40
*Bacillus subtilis*

All antibacterial assays were carried out in a laminar flow cabinet using the protocol described below. Growth or no-growth was assessed visually and by ELISA reader. The endpoint is reported as the minimum dilution (calculated also in μg/mL for the more potent fractions) required to totally inhibit growth over the 24 hr treatment period.

Method
1) A starter culture was set up by scraping a tip through a frozen aliquot of bacterial culture and placing in 10 mL of Columbia broth within a falcon tube. This was then placed in the bacterial shaker at 37° C. at 210 rpm overnight.
2) A blank reading was made on the spectrophotometer at 600 nm using 210 of Columbia broth. A reading of 200 μL of the starter culture was then taken.
3) In calculations, a final concentration of 0.005 was desired. The formula used for dilution of x mL starter was: x*A600=0.005*desired volume
4) 90 uL of MeOH was added to each well of a 96 well flat bottomed plate. 10 μL of sample was added to the top well and diluted 1:10 down the plate. Alternatively the top rows were left empty of MeOH and 100 μL of sample was added and then diluted at 1:10 down the plate.
5) The plates were then left to dry in a biological safety cabinet for 2-3 hours or until all solvent had evaporated off the plate.
6) 100 μL of diluted bacterial culture was then added to each well of the plate. The plate was then placed in the bacterial incubator at 37° C. overnight. The following day the plate was scored under the microscope for inhibition (clear solution indicating 100% inhibition compared with turbid solution for controls) and aggregation. For quantitation, plates were read at 405 nm (ELISA).

Nematicidal Screening

An anthelmintic bioassay, applicable to all parasitic nematodes with free-living life cycle stages, was used as a screen to detect activity and potency of crude extracts from *Acronychia* species against parasitic nematodes. The assay determines the effects of test extracts on larval development and follows the method described by Gill et al. (1995) *Int. J. Parasitol.* 25: 463-470.

Briefly, in this assay eggs of the nematode *Haemonchus contortus* (McMaster strain) were applied to the surface of an agar matrix containing the test sample and allowed to develop through to the L3, infective stage (6 days). At this time the stage of larval development reached and any unusual features (deformity, paralysis, toxicity) were noted by microscopic examination. To determine potency of the extracts, a series of two-fold dilutions of the parent extract are used and the, readout from this assay is a dilution titre.

Anti-inflammatory and Neuroprotectant Assay
Background

Production of nitric oxide and the pro-inflammatory cytokine TNF are associated with oxidative stress and inflammatory processes in general, and are increasingly implicated in the development of age-related neurological conditions, including Alzheimer's disease. An assay system to measure LPS or interferon-γ induced production of nitric oxide in N-11 murine microglial cells can be used to identify fractions and compounds with anti-inflammatory, neuroprotective and antioxidant activity. The "gold standards" for comparison in this assay are the bioflavonoids, apigenin and diosmetin.

Method
Cell Maintenance

N-11 microglia were grown in 175 cm² flasks on Dulbecco's Modified Eagle's Medium (DMEM) (Invitrogen) containing 5% fetal bovine serum (FBS) (Invitrogen) and 2 mM L-glutamine (Invitrogen) in addition to 1% streptomycin and penicillin antibiotic solution (Invitrogen). All cell lines were maintained in 5% $CO_2$ at 37° C.

Concentration of Cells

Once the cells had grown to confluence within the culture flask, they were removed using a rubber policeman, as opposed to trypsin treatment which is known to be responsible for removing membrane-bound receptors such as RAGE. The cell suspension was then concentrated by centrifugation for 3 minutes at 900×g and resuspended in a small volume of DMEM containing 0.1% FBS.

Cell Count

Equal volumes of resuspended cell solution and Trypan blue (0.1%) were mixed to a total volume of 20 µL. Half of the mix was placed onto a Neubauer counting slide. Sixteen squares of equal size were viewed and counted under a microscope. The number of cells per microliter of cell solution was calculated, by using the following equation: cell count×2 (dilution factor for Trypan blue)×10(1/100 of total volume counted)=number of cells per microliter.

Dispensing of Cells into Plates

Once the concentration of cell suspension was determined, the volume of media was adjusted to the required concentration. This was achieved by dividing total number of cells required by the number of cells per microliter. 100 µL of cell suspension was administered to each well of a 96-well plate to give a desired cell total of $5\times10^4$ cells per well. For experiments using 6-well plates, $1.2\times10^6$ cells per well were distributed into each well with a final total volume of 2 mL per well. For experiments using 24-well plates, $3\times10^5$ cells per well were distributed into each well with a final total volume of 1 mL per well. Plates were centrifuged at 500×g for 5 minutes to allow even distribution.

Activation of Cells

Following the dispensing of cells into plates, plates were incubated overnight at 37° C. to allow for settlement and attachment to the bottom of the wells. Before activation, conditioned media was replaced with fresh DMEM containing 0.1% FBS to minimize the effect, of growth during experimentation.

Lipopolysaccharide

A stock solution of 1000 µg/mL of *E. coli* LPS (serotype 0127:B8) in sterile PBS was used for cell dilutions. Concentrations of LPS ranging from 0.1 µg/mL to 100 µg/mL were used for the construction of a dose-dependent activation curve. A concentration of 10 µg/mL was used to activate cells in assays with extract's.

Interferon-γ

A stock solution of 1000 U/mL of murine IFN-γ (Lot #10098) was used in conjunction with DMEM with 0.1% FBS. A dose-dependent activation curve was constructed using concentrations of IFN-γ ranging from 0.1 U/mL to 500 U/mL. A concentration of 10 U/mL was used to activate cells in assays with extracts.

Activation of Cells for Assays with Extracts

Due to the inconsistent nature of LPS in activating cells, a combination of 10 µg/mL of LPS and 10 U/mL of IFN-γ was used to activate cells for assays with extracts.

Nitric Oxide Determination

Nitric oxide was determined by the Griess reagent quantification of nitrite, one of its stable reaction products. The Griess reagent was made up of equal volumes of 1% sulfanilamide and 0.1% napthyethylene-diamine in 5% HCl, and in the presence of nitrite forms a violet colour. A standard curve using known concentrations of sodium nitrite was constructed, and the absorbance of each sample was measured at 545 nm using a Wallac VICTOR$^3$ V Multilabel Counter (Perkin Elmer). 75 µL of supernatant from each activated well was transferred to a fresh 96-well plate and mixed with equal volumes of Griess reagent. Absorbance was measured, enabling the calculation of nitrite concentration from the sodium nitrite standard curve.

Alamar Blue Cell Viability Assay

Alamar blue is a fluorescent redox indicator used to measure cell viabilities. It involves the cellular reduction of resazurin by cellular mitochondrial enzymes, yielding a soluble product (resorufin), which is directly proportional to cell number. Cells were incubated with 100 µL per well of a 1% resazurin and DMEM (0.1% FBS) solution for 2 hours at 37° C. in 96-well plates. The total volume was adjusted for 24-well plates so that each well was incubated with 500 µL. Fluorescence was examined at 545/595 nm and expressed as a percentage of the control cells, following the subtraction of background readings.

Anticancer Activity Assay

Preliminary Cell Screening of Crude Extracts

Overview

The potency of ethanolic crude extracts is assessed against 5 cell-lines (4 tumour-lines and one normal human cell-line) in 96-well plate format. $IC_{50}$ values are calculated from 7 serial 10-fold dilutions on the 5 cell lines.

Method

The normal cells are primary human fibroblasts (NFF). The tumour cell lines used are MM418c5 melanoma (a pigmented cell line, to detect depigmenting agents), MCF-7 breast cancer, CI80-13S ovarian cancer (cisplatin-resistant; highly sensitive to mitochondrial drugs) and LnCAP prostate cancer line.

1. The cells are sparsely seeded and allowed to grow in tissue culture medium (RPMI1640+10% FCS+pen/strep) for 5-7 days to provide clonogenic type cell survival data.
2. The amount of cell suspension required to give 4000 cells per volume of 100 µL was calculated. This required cell suspension was mixed with tissue culture medium (with tyrosine added) to make up to the required volume.
3. The cell suspension was plated out at 100 µL per well into flat-bottomed 96-well tissue culture plates, before being placed into a 37° C., 5% $CO_2$, humidified incubator overnight.
4. 2 µL of the required fraction was then placed into the top well (row A) of a plate and mixed using a pipette before being serially diluted 1:10 down the plate to row G.
5. The plates were incubated again at 37° C. for 3-4 days before being assessed under a light microscope for cellular viability and morphological changes, particularly depigmentation and hyper-pigmentation of cells.

Preliminary Cell Screening of S1/S2 Fractions

Method for Mixed Cell Plates

1. Four different cell lines [NFF, MCF7, MM96L (melanoma) and K562 (leukemia)] suspended in tissue culture medium (RPMI1640+10% F.CS+pen/strep) were counted.
2. The amount of cell suspension required to give 1000 MM96L, 2000 K562, 3000 MCF7, and 5000 NFF per volume of 100 µL was calculated. This required cell suspension from each cell line was mixed together and tissue culture medium added to make up to the required volume.
3. The mixed cell suspension was plated out at 100 µL per well into flat-bottomed 96-well tissue culture plates, before being placed into a 37° C., 5% $CO_2$, humidified incubator overnight.

4. 2 µL of the required sample was then placed into the top well (row A) of a plate and mixed using a pipette before being serially diluted 1:10 down the plate to row G.
5. The plates were incubated again at 37° C. for 3-4 days before being assessed under a light microscope for cellular viability and morphological changes.

Method for MM418c5 Cell Plates

6. The MM418c5 melanoma cell line suspended in tissue culture medium (RPMI1640+10% FCS+pen/step+250 µg/mL Tyrosine) was counted.
7. The amount of cell suspension required to give 4000 cells per volume of 100 µL was calculated. This required cell suspension was mixed with tissue culture medium (with tyrosine added) to make up to the required volume.
8. The cell suspension was plated out at 100 µL per well into flat-bottomed 96-well tissue culture plates, before being placed into a 37° C., 5% $CO_2$, humidified incubator overnight.
9. 2 µL of the required sample was then placed into the top well (row A) of a plate and mixed using a pipette before being serially diluted 1:10 down the plate to row G.
10. The plates were incubated again at 37° C. for 3-4 days before being assessed under a light microscope for cellular viability and morphological changes, particularly depigmentation and hyper-pigmentation of cells.

Definition of Flavour and Fragrance Components

Background

Solid-phase microextraction (SPME) is a sample preparation and sample introduction method in which analytes partition from a sample into a polymer, coated on a fused silica rod of typically 1 cm length by 100 µm diameter. The fibre is fastened into the end of a fine stainless steel tube contained in a syringe-like device, and protected by an outer stainless steel needle. The device's plunger is depressed to expose the fibre to the sample matrix, retracted at the end of the sampling time, and then depressed again to expose the fibre to a desorption interface for analysis by GC-MS. SPME provides an alternative to headspace GC for analysis of volatiles in a wide range of situations (Pawlisyzn J 1999: Applications of Solid Phase Microextraction, Royal Society of Chemistry).

Method

Frozen fruit of *Acronychia acidula* was chopped into approximately 5 mm cubes and gently bruised in a mortar and pestle to disrupt the outer cells and to release volatile components. The chopped fruit was then transferred immediately to a glass container fitted with a septum. A commercial SPME fibre holder (Supelco Analytical, USA) and fibre (polydimethylsiloxane, 100 µm film 57310-U) was inserted through the septum and the plunger used to lower and expose the fibre to the volatile mixture in the glass container for 15 minutes. The fibre was then retracted and later desorbed and analysed by GC-MS.

Example 1

Crude Extract Preparation

Frozen fruit of *Acronychia acidula* was sliced into approximately 5 mm cubes, generously covered with ethanol (~2 L) and shaken overnight. This extract was then filtered and most of the solvent removed by rotary evaporation to afford an aqueous concentrate (the crude extract).

Example 2

First Fractionation Using a Silica Column (S1)

Preparation of Extract for S1 Column 1. 200 mL to 1 L of milli-Q water was added to dried or concentrated crude extract (extract should have all solvents apart from water dried off, the volume of water used was dependant on amount of extract)
2. The same volume of ethyl acetate was added to the sample and mixed before transferring to a separating funnel. This is shaken for ~30 seconds, with care taken to release the pressure in the funnel frequently.
3. The two layers were allowed to separate then collected separately.
4. The water layer was placed back into the funnel then steps 2-3 repeated.
5. A 1 mL sample from each layer was collected and stored, then the individual layers dried on the rotary evaporator and weighed.
6. The ethyl acetate layers were combined and dissolved in a small amount of ethyl acetate solvent before being stored at 4° C. or −20° C. until required for silica column chromatography.

Method for Pilot Silica Column (S1)

Column Preparation:

1. 1 g of Merck Silica Gel 60 (0.063-0.2 mm) was weighed into a 100 mL beaker.
2. Silica was covered with ~10 mL of petroleum spirit and mixed thoroughly with a spatula.
3. The silica was poured directly after stirring into a glass column of 1 cm internal diameter, the tap of the column was opened and the silica allowed to run through for a couple of minutes.
4. The tap was turned off and the silica allowed to settle for at least one hour (preferably overnight). The top of the column was covered with an air-tight seal to prevent solvent from evaporating.
5. After settling, any bubbles in the column were gently tapped out. If any large air-bubbles were present, the entire bed was stirred up and allowed to re-settle.
6. The height of the column was recorded (approx. 3 cm).

Sample Preparation:

7. Approximately 150 mg of the appropriate concentrated crude extract was measured into a small round bottom flask.
8. The sample was dried by rotary evaporation and the weight recorded.
9. The dried sample was re-dissolved in ethyl acetate in a volume equal to 2 times the mass of the sample.
10. Petroleum spirit was then added to the sample in small volumes (20-50 µL) until the sample started to precipitate out of solution. The precipitate was re-dissolved by adding a small amount of ethyl acetate. The volume of pet spirit added was recorded. The load volume should always be under 2 mL.
11. A 200 µL pipette was used to accurately measure out $1/6^{th}$ of the of the load (~20 mg). This was placed in the last well in a set of 24 wells (two rows) of a 2 mL 96 well plate (polypropylene, chemically resistant).

Sample Fractionation:

12. 4 mL of each of the following solvent ratios was prepared as shown in Table 1:

TABLE 1

| Solvent Mix | Pet. Spirit | Ethyl Acetate | Methanol |
|---|---|---|---|
| 1 | 8 | 1 | |
| 2 | 3 | 1 | |
| 3 | 2 | 1 | |
| 4 | 1 | 1 | |
| 5 | 1 | 2 | |
| 6 | 1 | 4 | |
| 7 | 0 | 1 | |
| 8 | | 99 | 1 |
| 9 | | 95 | 5 |
| 10 | | 90 | 10 |
| 11 | | 0 | 100 |

13. The solvent in the column was allowed to elute until the level of the solvent was just above the silica.
14. The remaining load was gently run down the sides of the column using a 1 mL Pasteur pipette, taking care to ensure the load was even. The sides of the column were then rinsed with a small amount of solvent to remove any load.
15. The tap was opened and the load allowed to move onto the column.
16. Using a Pasteur pipette as before, the first solvent mix was added to the column with care taken not to disturb the silica.
17. The solvent was allowed to move through the column, and for each solvent two 2 mL fractions were collected sequentially into the 2 mL 96-well plate.
18. The above was repeated for each solvent ensuring that the previous solvent had eluted to the top of the column before addition of new solvent.
19. The fractions in the 96-well plate were dried by blowing nitrogen over them.
20. 400 μL of ethanol was added to each dried fraction and mixed using a pipette to dissolve the samples. 100 μL of each sample was transferred to each of 3 round-bottom 96-well plates.

Example 3

Method 2 for the Fractionation of Crude Extract (S2)

Extraction:
1. Fruit of *A. acidula* (5090 g) was extracted once with ethanol (5.0 L) for 24 h and filtered to provide 3025 g of residue. This residue was ground using a Phillips "Super blender" to give well divided material and extracted twice with EtOH (4.0 L and 3.0 L) for 24 h at ambient temperature.
2. Aliquoted (2 mL) samples were kept from each extract: EB 1328-EtOH-1 (from 6400 mL), EB1328-EtOH-2 (from 4250 mL), EB1328-EtOH-3 (from 2400 mL).
3. The extracts were combined and ethanol was removed by rotary evaporation. The residue (~1600 mL) was extracted with EtOAc (5×650 mL). The EtOAc was removed by rotary evaporation to give 53 g of dark oily material. The following aliquoted (2 mL) samples were kept:
   Aqueous phase after extraction (from 1630 mL) was labelled as: EB1328-H$_2$O.
   Ethyl acetate extract (from 3260 mL) was labelled as EB1328-EtOAc.

Silica Column: S2

The final extract (53 g) was dissolved in EtOAc (150 mL) and silica (about 106 g) was added in order to prepare a homogeneous suspension. Hexane (100 mL) was added and the solvents were removed. Residual mixture was dried at 50° C./20 Torr for 1 h. The column was packed with silica and the obtained dry load was added to the top of the column (424 g of silica, column diameter 10 cm×13.0 cm and dry load on silica 3.0 cm, total ~1200 mL), which was eluted, using vacuum suction, with the solvents indicated in Table 2 and collected fractions as shown in the Table 3.

TABLE 2

Solvent mixtures for S2.

| Solvent | PS | EtOAc | MeOH | Volume, mL | No fractions |
|---|---|---|---|---|---|
| 1 | 8 | 1 | 0 | 1800 | 1-2 |
| 2 | 3 | 1 | 0 | 1200 | 3-4 |
| 3 | 2 | 1 | 0 | 1200 | 5-6 |
| 3 | 1 | 1 | 0 | 1200 | 7-8 |
| 5 | 1 | 2 | 0 | 1200 | 9-10 |
| 6 | 1 | 4 | 0 | 1200 | 11-12 |
| 7 | 0 | 1 | 0 | 1200 | 13-14 |
| 8 | 0 | 99 | 1 | 1200 | 15-16 |
| 9 | 0 | 95 | 5 | 1200 | 17-18 |
| 10 | 0 | 90 | 10 | 1200 | 19-20 |
| 11 | 0 | 0 | 100 | 1200 | 21-22 |

PS = petroleum spirit

Collected fractions were dried and transferred into 4.5 mL vials as solutions in a suitable solvent (see Table 3). The analytical samples of fractions were prepared by dilution of 45 μL amount of fraction solutions to 1 mL of MeOH. Large fraction (EB1328-S2-4) was left for fractional crystallization to provide three samples (see Table 3).

TABLE 3

List of collected fractions EB1328-S2.

| ## | Fraction title | Fraction volume, mL | Solvent for samples | Tare + sample, g | Tare, g | Sample, g |
|---|---|---|---|---|---|---|
| 1 | EB1328-S2-1 | 600 | Hexanes + acetone | 208.900 | 207.615 | 1.285 |
| 2 | EB1328-S2-2 | 600 | Hexanes + acetone | 211.070 | 207.950 | 3.120 |
| 3 | EB1328-S2-3 | 600 | acetone | 210.835 | 209.685 | 1.150 |
| 4-1 | EB1328-S2-4solid impure | n/a | acetone | 9.768 | 5.442 | 4.326 |
| 4-2 | EB1328-S2-4solid | n/a | acetone | 5.535 | 5.435 | 0.100 |
| 4-3 | EB1328-S2-4solid | 600 | acetone | 6.210 | 5.455 | 0.755 |
| 4-4 | EB1328-S2-4ml | n/a | acetone | 49.715 | 46.180 | 3.535 |
| 5 | EB1328-S2-5 | 600 | acetone | 209.270 | 207.950 | 1.320 |
| 6 | EB1328-S2-6 | 600 | acetone | 331.340 | 327.760 | 3.580 |
| 7 | EB1328-S2-7 | 600 | acetone | 210.155 | 209.685 | 0.470 |
| 8 | EB1328-S2-8 | 600 | acetone | 343.635 | 338.300 | 5.335 |
| 9 | EB1328-S2-9 | 600 | acetone | 209.110 | 207.950 | 1.160 |
| 10 | EB1328-S2-10 | 600 | acetone | 345.070 | 341.360 | 3.710 |
| 11 | EB1328-S2-11 | 600 | acetone | 210.250 | 209.685 | 0.565 |

TABLE 3-continued

List of collected fractions EB1328-S2.

| ## | Fraction title | Fraction volume, mL | Solvent for samples | Tare + sample, g | Tare, g | Sample, g |
|---|---|---|---|---|---|---|
| 12 | EB1328-S2-12 | 600 | acetone | 342.620 | 339.610 | 3.010 |
| 13 | EB1328-S2-13oil | 600 | acetone | 144.510 | 141.925 | 2.585 |
| 13-1 | EB1328-S2-13S | n/a | $H_2O$ | 7.151 | 5.471 | 1.680 |
| 14 | EB1328-S2-14oil | 600 | acetone | 148.660 | 146.515 | 2.145 |
| 14-1 | EB1328-S2-14S | n/a | $H_2O$ | 6.476 | 5.446 | 1.030 |
| 15 | EB1328-S2-15 | 600 | acetone | 340.155 | 340.070 | 0.085 |
| 16 | EB1328-S2-16 | 600 | acetone | 337.315 | 336.815 | 0.500 |
| 17 | EB1328-S2-17 | 600 | Acetone + MeOH | 341.495 | 340.995 | 0.500 |
| 18 | EB1328-S2-18 | 600 | Acetone + MeOH | 341.555 | 340.870 | 0.685 |
| 19 | EB1328-S2-19 | 600 | Acetone + MeOH | 337.280. | 336.280 | 1.000 |
| 20 | EB1328-S2-20 | 600 | MeOH | 336.485 | 335.840 | 0.645 |
| 21 | EB1328-S2-21 | 600 | MeOH | 340.625 | 339.890 | 0.735 |
| 22 | EB1328-S2-22 | 600 | MeOH | 338.070 | 334.665 | 3.405 |

Recovery of material from EB1328_S2: 48.4
48.4 g/~53.0 g × 100 = 91.3%.
Total

The fractions EB1328-S2-4 (12.42 g), EB1328-S2-13 and EB1328-S2-14 solidified on evaporation and EB1328-S2-4 was re-crystallized from hexane/acetone to provide three fractions (solid—EB1328-S2-4solid, impure solid—EB1328-S2-4solid impure, and oil—EB1328-S2-4mL), which were analysed by GCMS. Fraction EB1328-S2-solid according to GCMS is a single compound with retention time 28.20 min. Fractions EB1328-S2-4solid impure and EB1328-S2-4 mL, excluding volatile compounds, consist of four main components with retention times ($R_f$) 7.06, 27.96, 28.20, 33.71 min. The major component for both EB1328-S2-4solid-impure and EB1328-S2-4 mL fractions has $R_t$ 27.96 min with concentration about 77% and 63% respectively.

The fractions EB1328-S2-13 and EB1328-S2-14 were filtered for collection and the formed precipitates were washed with acetone. According to $^J$H and $^{13}$C NMR, the solid collected from both fractions was citric acid [Olennikov et al. Chem. Nat. Compounds, 2005, 41(4); p 467-468].

GCMS Analysis.

Chromatograph: Shimadzu GC-17A Ver.3, mass-spectrometer: MS QP5050A, ionization at 70 eV, column: DB-5 ms—diameter 0.32 mm×30 m×0.25 μm, carrier-gas: He, total flow 32.2 mL/min, column flow 1.3 mL/min, injector temperature: 250° C. Standard Program: 1 min at 140° C., followed by a temperature increase of 5° C./min and left for 30 min at 290° C.

Example 4

Results from Preliminary Studies from Crude Extracts

Crude ethanolic extracts of fruit of *Acronychia acidula* and three other *Acronychia* species (*A. aberrans, A. acronychioides* and *A. crassipetala*) were screened in a number of assays to characterize their antioxidant, antibacterial, anti-inflammatory and anticancer activities (Table 4). The crude extracts were assayed using DPPH method as an assay for radical scavenging, Lipid peroxidation assay, Antibacterial growth assay, and preliminary anticancer screening assays as described above.

TABLE 4

Summary of results from preliminary screening of crude extracts of *Acronychia* species

| Species | EB code | Antioxidant[1] Radical scavenging (μmol eq g $DW^{-1}$) | Antioxidant Lipid peroxidation (μM $CEOOHh^{-1}$) | Antibacterial Growth inhibition ($IC_{50}$, μg $ml^{-1}$) | Anti-inflammatory[2] iNOS ($IC_{50}$, mg $ml^{-1}$) | Anticancer[3] Inhibition of cell growth ($IC_{50}$, mg $ml^{-1}$) | Anthelmintic[4] Inhibition of larval development (Titre) |
|---|---|---|---|---|---|---|---|
| *A. acidula* | 1328 | ORAC = 472 DPPH = 35 | EB1328 = 1.17 Control = 9.65 | *S. salivarius* <100 | 0.05 | CI80-13s = 0.31 LnCAP = 0.85 MCF7 = 0.18 MM418c5 = 0.80 NFF = 1.36 | 32 |
| *A. acidula* | 1281 | ORAC = 510 DPPH = 44 | n/a | *B. subtilis* 50 | 0.06 | n/a | n/a |
| *A. aberrans* | 1283 | ORAC = 833 DPPH = 61 | n/a | *B. subtilis* <100 | 0.03 | MM418c5 = 0.72 NFF = 1.43 | 64 |
| *A. acronychioides* | 1284 | ORAC = 467 DPPH = 58 | n/a | *B. subtilis* 80 | 0.01 | MM418c5 = 1.1 NFF = 1.04 | 16 |
| *A. crassipetala* | 1282 | ORAC = 773 DPPH = 47 | n/a | *B. subtilis* 50 | 0.02 | MM418c5 = 0.76 NFF = 1.22 | 32 |

[1]Data expressed in trolox equivalents for ORAC assay and catechin equiValents for DPPH assay
[2]Inhibition of LPS-induced nitric oxide production in N11 microglial cells
[3]Cell-lines: CI80-13s = ovarian; LnCAP = prostate; MCF7 = breast; MM418c5 = melanoma; NFF = normal
[4]Inhibition of development of *Haemonchus contortus* larvae expressed as an the last dilution at which activity was observed in a 2-fold serial dilution Further studies then focussed on *A. acidula* as the species for activity-guided isolation to identify specific 'active' fractions in the fruit because of its availability from small-scale commercial plantations.

Example 5

Identification of Bioactive Fractions

Flash chromatography on silica of an ethyl acetate extract of *Acronychia acidula* (see S1 method in protocols above)

was used as the first stage in deconvoluting the complex mixture in the crude extract to identify biologically active fractions. Specific fractions with moderately potent antibacterial and anticancer activity were identified (Table 5), while strong anti-inflammatory/antioxidant activity (<0.05 mg mL$^{-1}$) was present in many of the fractions.

TABLE 5

Results from screening of S1 fractionated extract of *A. acidula* (EB1328)

| Fraction | Antibacterial[1] Growth inhibition of *S. salivarius* | Anti-inflammatory[2] iNOS (IC$_{50}$, mg mL$^{-1}$) | Anticancer[3] Toxicity in mixed cells (mg mL$^{-1}$) | Anticancer Toxicity in MM418c5 cells (mg mL$^{-1}$) |
|---|---|---|---|---|
| 1 | 1 | 0.492 | 0.0002 | 0.002 |
| 2 | 2 | 0.050 | 0.02 | 0.02 |
| 3 | 3 | 0.054 | 0.02 | 0.02 |
| 4 | 2 | 0.050 | 0.02 | 0.02 |
| 5 | 3± | 0.050 | 0.02 | 0.02 |
| 6 | 3± | 0.054 | 0.02 | 0.02 |
| 7 | 2 | 0.050 | 0.02 | 0.02 |
| 8 | 2± | 0.050 | 0.02 | 0.02 |
| 9 | 2± | 0.046 | 0.02 | 0.02 |
| 10 | 1± | 0.046 | 0.02 | 0.02 |
| 11 | 2± | 0.042 | 0.02 | 0.02 |
| 12 | 2 | 0.050 | 0.02 | 0.02 |
| 13 | 0 | 0.042 | 0.02 | 0.02 |
| 14 | 1 | 0.046 | — | 0.02 |
| 15 | 1 | 0.071 | — | 0.02 |
| 16 | 1± | 0.050 | — | 0.02 |
| 17 | 1 | 0.054 | — | 0.02 |
| 18 | 2 | 0.058 | — | 0.02 |
| 19 | 1 | 0.088 | — | 0.02 |
| 20 | 0 | 0.434 | — | 0.02 |
| 21 | 0 | 0.054 | 0.02 | 0.02 |
| 22 | 0 | 0.042 | <0.02 | 0.02 |
| Load | 1 | 0.046 | 0.02 | 0.02 |

[1]Minimum dilution required to totally inhibit growth of *S. salivarius* at 24 hr, data refers to first row in test plate
[2]Inhibition of LPS-induced nitric oxide production in N11 microglial cells
[3]Comprises mixture of 4 cell-lines: MM96L melanoma; K562 leukaemia; MCF7 breast; normal Subsequent larger scale fractionation (S2) was undertaken to more accurately quantify the antibacterial and anticancer activity in *A. acidula*.

TABLE 6

Antibacterial and anticancer endpoints in S2 fractionated extract of *A. acidula* (EB1328)

| Fraction | Antibacterial[1] Endpoint for growth inhibition of *S. salivarius* (μg mL$^{-1}$) | Anticancer[2] Endpoint for toxicity in mixed cells (μg mL$^{-1}$) | Anticancer[2] Endpoint for toxicity in MM418c5 cells (μg mL$^{-1}$) |
|---|---|---|---|
| 1 |  | 23 | 23 |
| 2 |  | 57 | 57 |
| 3 | 102 | 230 | 21 |
| 4 | 67 | 64 | 64 |
| 5 | 117 | 264 | 264 |
| 6 |  | 716 | 716 |
| 7 |  | 94 | 94 |
| 8 |  | 97 | 97 |
| 9 |  | 232 | 232 |
| 10 |  | 742 | 67 |
| 11 | 502 | 113 | 113 |
| 12 |  | 602 | 602 |
| 13 |  | 517 | 517 |
| 14 |  | 429 | 429 |
| 15 |  | n/a | 17 |
| 16 |  | 100 | 100 |
| 17 |  | 100 | 100 |
| 18 | 609 | 137 | 137 |
| 19 |  | 200 | 200 |
| 20 |  | 129 | 129 |
| 21 |  | 147 | 147 |
| 22 |  | 681 | 681 |

[1]Minimum dilution required to totally inhibit growth of *S. salivarius* at 24 hr, data expressed in μg mL$^{-1}$ of fraction
[2]Endpoint is the minimum concentration at which all cells in a well were killed Example 6

To more specifically identify fractions and compounds with the antibacterial activity, 10 g of freeze-dried powder of *A. acidula* (EB1328) was extracted three times with petroleum spirit (3×50 mL). Combined extracts were concentrated to dryness in a rotary evaporator and resulting residue (0.248 g) was dissolved in methanol (HPLC grade) at 10 mg/mL and separated by HPLC. HPLC purification was carried out using Gracevydac C18 reversed phase column (100×4.60 mm, 120 A) at a flow rate of 0.5 mL/min of methanol/water (80/20 v/v and then gradient to 100% of methanol). HPLC fractions (0.5 mL) were collected using Gilson fraction collector FC204 and tested for antibacterial activity against *Streptococcus salivarius*. Results showing fractions active in the antibacterial test are presented in Table 7.

TABLE 7

HPLC fractions from *Acronychia acidula* (EB1328) showing inhibitory activity against *Streptococcus salivarius*

| Fraction number | Amount of fraction (μL) giving 100% inhibition of growth of *S. salivarius** |
|---|---|
| 16 | 100 |
| 17 | 100 |
| 18 | 10 |
| 19 | 10± |
| 20 | 10 |
| 21 | 10± |
| 22 | 10Ag |

*Ag = aggregation,
±= partial inhibition

To further identify active antibacterial components in *A. acidula*, fractions correlating to the three dominant peaks (15.0-18.0, 18.1-20.0 and 20.1-22.8 retention times) were pooled separately. The purity of the collected HPLC fractions was confirmed by running samples with an alternate HPLC solvent system (0.5 mL/min of methanol/water 70/30 mL/min) and by GC-MS analysis. On the basis of HPLC analysis, peak purity was 85-95%.

Active fraction 22 (coded as EB1328-QL02) was determined by GC-MS to be pure material with M$^+$ 370.5. $^1$H and 13C NMR spectra were recorded and are shown in Table 8. $^1$H and $^{13}$C NMR proved this structure to be known compound 3-(4-farnesyloxyphenyl)propionic acid (CAS No. 126269-87-2); this structure was designated with identifier EBC111.

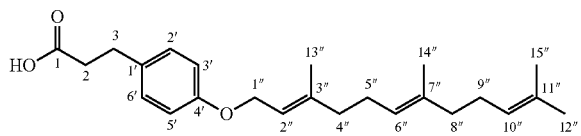 [SMILES: CC(C)=CCC/C(C)=C/CC/C(C)=C/COc1ccc(CCC(=O)O)cc1]

TABLE 8

NMR Data in CDCl₃ at 125/500 MHz.

| No. | $^{13}$C | $^{1}$H | Multiplicity (J in Hz) |
|---|---|---|---|
| 1 | 178.5 | | |
| 2 | 35.8 | 2.66 | t (7.8) |
| 3 | 29.8 | 2.91 | t (7.8) |
| 1' | 132.1 | | |
| 2',6' | 129.2 | 7.12 | d (8.7) |
| 3',5' | 114.7 | 6.86 | d (8.7) |
| 4' | 157.4 | | |
| 1" | 64.9 | 4.52 | d (6.5) |
| 2" | 119.6 | 5.50 | td (6.5, 1.2) |
| 3" | 141.1 | | |
| 4" | 39.6 | 2.09 | m |
| 5" | 26.2 | 2.14 | m |
| 6" | 123.7 | 5.12 | m |
| 7" | 135.4 | | |
| 8" | 39.7 | 1.98 | m |
| 9" | 26.7 | 2.07 | m |
| 10" | 124.3 | 5.10 | m |
| 11" | 131.3 | | |
| 12" | 25.7 | 1.69 | d (1.0) |
| 13" | 16.7 | 1.74 | s |
| 14" | 16.0 | 1.61 | |
| 15" | 17.7 | 1.61 | |

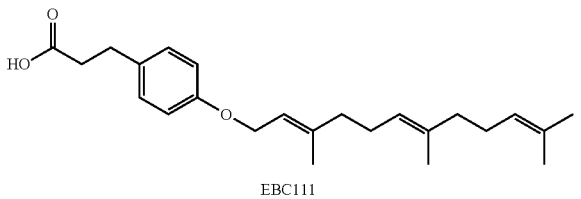

EBC111

Molecular Weight = 370.54
Molecular Formula = C₂₄H₃₄O₃

Active fraction 20 (Table 7) (3.3 mg) was purified by HPLC to give 1.17mg of pure compound suitable for NMR analysis. This fraction (coded EB1328-QL01) was determined by LCMS to be close to pure material with m/z 423.5 M+Na⁺. ¹H NMR (500 MHz, CHLOROFORM-d) δ ppm 1.57 (s, 6 H), 1.65 (s, 3 H), 1.69 (s, 3H), 1.92-1.96 (m, 2 H), 2.00-2.06 (m, 4 H), 2.07-2.13 (m, 2 H), 2.64 (t, J=7.5 Hz, 2 H), 2.88 (t, J=7.5 Hz, 2 H), 3.83 (s, 3 H), 4.56 (d, J=6.2 Hz, 2 H), 5.07 (q, J=7.1 Hz, 2 H), 5.48 (t, J=6.2 Hz, 1 H), 6.69 (d, J=7.8 Hz, 1 H), 6.71 (s, 1 H), 6.77 (d, J=7.8 Hz, 1 H). ¹³C NMR (126 MHz, CHLOROFORM-d) δ ppm 16.00, 16.67, 17.68, 25.69, 26.22, 26.71, 30.32, 35.34, 39.56, 39.68, 55.84, 65.95, 111.85, 113.38, 119.91, 119.99, 123.77, 124.34, 131.32, 135.35, 140.52, 143.42, 146.79, 149.41, 176.09. ¹³C NMR demonstrated the isolate to be a previously unreported structure related to EBC111, this new structure was designated as EBC125.

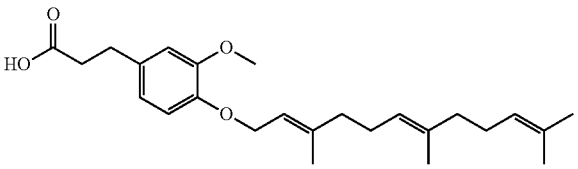

EBC125
Molecular Weight = 400.56
Molecular Formula = C₂₅H₃₆O₄

The separated fractions and the two compounds isolated from *A. acidula* (EB1328) were further tested for activity against *S. salivarius* (Table 9).

TABLE 9

Inhibitory activity against *Streptococcus salivarius* of HPLC fractions and two pure compounds isolated from *Acronychia acidula* (EB1328).

| Fraction number (isolate code) | Amount of fraction (μl) giving 100% inhibition of growth of *S. salivarius** |
|---|---|
| 17 | 100 |
| 18 | 10 |
| 19 | 10± |
| 20 | 10 |
| 21 | 10 |
| 20-3 | 10 |
| 20-4 (EBC125) | 1 |
| 22 (EBC111) | 10Ag |

*Ag = aggregation,
±= partial inhibition

Example 7

Identification of Flavour and Fragrance Components

Volatile components likely responsible for flavour and fragrance characteristics of *Acronychia acidula* fruit were determined by solid-phase microextraction (SPME) coupled to GC-MS as described above.

GC-MS analysis identified that three major volatiles were present:

1-Ethenyl-1-methyl-2,4-bis(1-methylethenyl)-cyclohexane 2,6-Di-tert-butylbenzoquinone Tetracontane-1,40-diol)

and recorded a further 6 minor volatiles (FIG. 1).

The invention claimed is:

1. A composition in the form of a cosmetic, product, said composition comprising a fragrance component comprising an extract from the fruit of *Acronychia acidula*, said extract comprising at least three of:

1-ethenyl-1-methyl-2,4-bis(1-methylethenyl)cyclohexane, 2,6-di-tert-butylbenzoquinone, 2,5-di-tert-butyl-1,4-benzoquinone, Tetracontane-1,40-diol, and 2,2,5,5-tetramethyl-bicyclo [6.3.0]undec-1(8)-enone;and wherein the cosmetic product is in the form of a face cream, body lotion, hand cream or foundation.

2. A cosmetic composition comprising as a component a composition comprising an extract from the fruit of *Acronychia acidula*, wherein the extract is obtained by a method comprising initial water or alcohol extraction and a subsequent ethyl acetate extraction; said cosmetic composition being in the form of a face cream, body lotion, hand cream or foundation.

\* \* \* \* \*